(12) United States Patent
Sutter et al.

(10) Patent No.: US 8,298,230 B2
(45) Date of Patent: Oct. 30, 2012

(54) COAGULATION FORCEPS WITH A HOLLOW SHAFT

(75) Inventors: Hermann Sutter, Gundelfingen (DE); Dirk Weitkamp, Waldkirch (DE)

(73) Assignee: Sutter Medizintechnik GmbH, Freiburg (DE)

( * ) Notice: Subject to any disclaimer, the term of this patent is extended or adjusted under 35 U.S.C. 154(b) by 1944 days.

(21) Appl. No.: 11/378,503

(22) Filed: Mar. 17, 2006

(65) Prior Publication Data
US 2006/0217708 A1 Sep. 28, 2006

(30) Foreign Application Priority Data
Mar. 24, 2005 (DE) .................... 20 2005 004 773 U

(51) Int. Cl.
*A61B 18/14* (2006.01)
(52) U.S. Cl. .............................. 606/51; 606/52; 606/207
(58) Field of Classification Search .............. 606/41–52, 606/174, 205–211
See application file for complete search history.

(56) References Cited

U.S. PATENT DOCUMENTS

| 4,049,002 | A | | 9/1977 | Kletschka et al. | |
|---|---|---|---|---|---|
| 5,190,541 | A | * | 3/1993 | Abele et al. | 606/46 |
| 5,217,460 | A | * | 6/1993 | Knoepfler | 606/52 |
| 5,322,055 | A | * | 6/1994 | Davison et al. | 601/2 |
| 6,210,411 | B1 | * | 4/2001 | Hofmann et al. | 606/52 |
| 2004/0068274 | A1 | * | 4/2004 | Hooven | 606/151 |
| 2005/0124987 | A1 | * | 6/2005 | Goble | 606/50 |
| 2005/0222602 | A1 | | 10/2005 | Sutter et al. | |

FOREIGN PATENT DOCUMENTS

| EP | 0 316 816 | 5/1989 |
|---|---|---|
| FR | 2 469 912 | 11/1979 |

* cited by examiner

*Primary Examiner* — Linda Dvorak
*Assistant Examiner* — Ronald Hupczey, Jr.
(74) *Attorney, Agent, or Firm* — Volpe and Koenig, P.C.

(57) ABSTRACT

Coagulation forceps (1) with a hollow shaft (2) and with a fixed forceps leg (3), set at an angle in reference to the hollow shaft (2) and provided with a gripping surface (3a) are provided, having a forceps leg (6) pivotally mounted in reference thereto at a pivot support (4). At the exterior or bottom side facing away from the pivotal forceps leg (6), a hollow profile (8) is provided for stiffening or reinforcing it, which has a mouth or entry opening (10) at the distal end of its interior longitudinal caving (9), i.e. is open and leads to a suction connection (12) so that suction can be applied via the hollow profile (8) in the distal end region of this forceps leg (3).

12 Claims, 2 Drawing Sheets

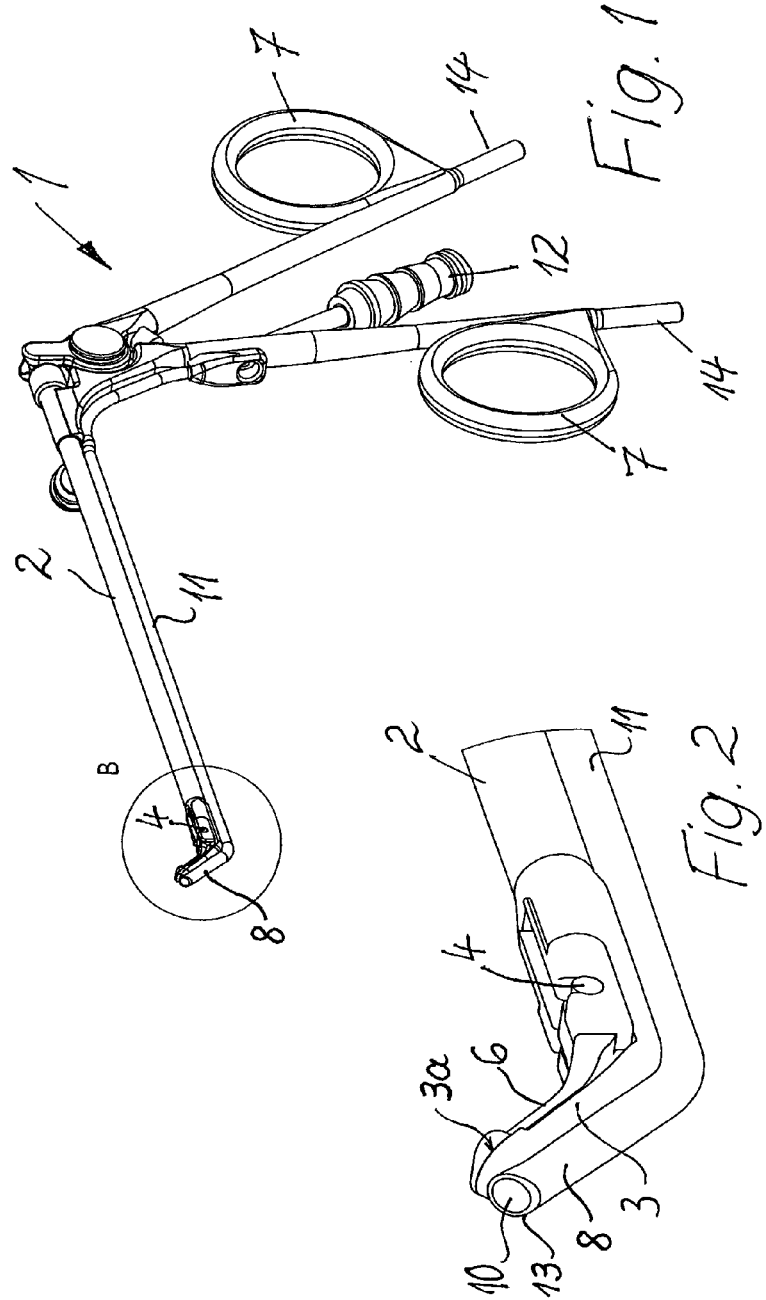

COAGULATION FORCEPS WITH A HOLLOW SHAFT

CROSS-REFERENCE TO RELATED APPLICATIONS

This application claims the benefit of German Application No. 20 2005 004 773.2, filed Mar. 24, 2005.

BACKGROUND

The invention relates to a pair of coagulation forceps with a hollow shaft and with a fixed forceps leg, positioned at an angle in reference to the hollow shaft, provided with a gripping surface, as well as a forceps leg in reference to the fixed forceps leg pivotal at a pivot support by way of a pivoting element.

Such coagulation forceps are known as hollow shaft instruments and have proven successful. Using the forceps legs, the tissue parts grasped by the respective gripping surfaces can be coagulated.

For use in very tight spaces, such as for example in the ear, in the nasal area, or in other tight body cavities, such coagulation forceps must be provided as space-saving a form as possible, which results in the risk of compromising stability.

SUMMARY

Therefore, the objective is to provide coagulation forceps of the type mentioned at the outset, in which stress, caused by movable forceps legs at the angled, fixed forceps leg, and which may also be increased based on the angle, can be well absorbed, i.e. sufficient stability of the angled, fixed forceps leg, can be achieved primarily, yet the forceps are still constructed as space-saving as possible.

In order to attain this objective, the invention provides for the fixed forceps leg to be reinforced or stiffened by a hollow profile at the exterior side facing away from the forceps leg or the underside, which is open in the end region of the forceps leg with its interior longitudinal cavity and which extends towards the hollow shaft and with an extension along the hollow shaft and which at the proximal end of the extension is provided with a suction connector. The coagulation forceps are embodied as bipolar coagulation forceps, and insulation is provided between the fixed forceps leg and the support for the movable forceps leg.

Therefore, the coagulation forceps can be provided as bipolar coagulation forceps with an appropriate insulation and here, primarily by the hollow profile, a stiff and stable embodiment of the angled fixed forceps leg results, without its dimension having to be increased beyond the desired measurements, and simultaneously providing the considerable advantage that at a distal, free end of the fixed forceps leg, suction can be applied, which is frequently necessary in the work area of coagulation forceps, generally being performed by an additionally introduced suction tube, with its additionally required space being saved by the arrangement according to the invention. Thus, the hollow profile arranged at the outside of the fixed forceps leg has a dual function, on the one hand, providing said forceps leg with reinforcement and a stiffening effect, so that it can appropriately absorb high stress, and, on the other hand, simultaneously transferring suction in the work area of the forceps leg, without the insertion of a separate suction tube being required.

Here, it is particularly advantageous for the hollow profile to end in the area of the distal free end of the fixed forceps end and extending therefrom over the entire longitudinal extension of the forceps leg. This way it is possible to achieve suction already at the outer-most distal end of the forceps leg and its gripping surface serving to grasp tissue and simultaneously to support or reinforce the fixed forceps leg up to its distal end.

The hollow profile and its extension can be connected or welded in one piece. Such a fixed, in particular, one-piece connection is possible because the hollow profile is arranged at the fixed forceps leg, and thus is not required to execute any pivotal motion in reference to the hollow shaft.

The entry opening at the open end of the hollow profile can be approximately flush with the distal end of the gripping surface of the fixed leg. This attains the objective of allowing suction to occur already at the exterior distal end of the gripping surface, with simultaneously the fixed forceps leg being supported and reinforced by the hollow profile to its free end.

The encircling rim of the entry opening into the hollow profile may be arranged in a plane forming an angle with the plane of the gripping surface, which is equal or smaller than 90°. Here, the rim of the entry opening of the hollow profile facing away from the gripping surface can be off-set backwards in reference to the end of the entry opening and the hollow profile together with the gripping surface, seen from the side, can be sloped or formed with a conically narrowing shape. Such a design in the mouth region of the hollow profile will facilitate the introduction of the fixed leg into a narrow opening.

The cross-section of the hollow profile may be circular or oval, with the circular shape being advantageous in its maximum opening surface.

In particular, at its distal end and/or its progression along the fixed forceps leg the hollow profile may be provided flattened and/or with an oval cross-section, with the larger dimension of the cross-section being arranged approximately parallel to the gripping surface and, if necessary, being approximately equivalent to the width of the gripping surface of the fixed forceps leg or having a smaller dimension in reference thereto. Thus, the given width of the gripping surface can be well utilized in order to house a hollow profile with a sufficiently large cross-section without requiring an increase of the overall dimensions beyond the desired measurements.

The hollow profile may be connected to the fixed leg in a fixed manner, in particular, soldered or welded. This way, not only a fixed connection can be achieved, tolerating temperature fluctuations, for example during sterilization, but a largely smooth exterior surface can be achieved as well, which is beneficial for manipulation and cleaning.

A further embodiment provides for the fixed forceps leg and the hollow profile to be connected in one piece and having a connection point to the hollow profile extending along the hollow shaft.

A particularly advantageous and useful embodiment of the invention may comprise the coagulation forceps being provided as bipolar coagulation forceps and that insulation is provided between the fixed forceps leg and the support for the movable forceps leg. Bipolar coagulation forceps allow a targeted and effective coagulation, which according to the invention can simultaneously be combined with suction, and, based on the form of the fixed forceps leg with sufficient stiffening by the hollow profile, enough space remains for the mounting the insulation.

The insulation can protect at least the not-angled part of the fixed forceps leg, and in particular is connected thereto. Generally, such a fixed angled forceps leg transfers, via an angle or a bend, into a part extending in the direction of the hollow shaft or being connected thereto. Due to the fact that generally the support for the pivotal forceps leg is also provided in this area, the insulation that is required for a bipolar embodiment of the pair of coagulation forceps can be allocated at this point as well.

Primarily in combinations of individual or several of the above-mentioned features and measures, coagulation forceps result, by which bleeding sites can be coagulated, so that simultaneously an endoscope can be inserted at the surgery site without reducing or hindering the view through the endoscope. By the suction connection at the extension of the hollow profile, for example in the area of the grip of the coagulation forceps, vacuum can be applied and thus the coagulated place can be suctioned clear so that the surgeon can clearly recognize where the blood exits and where coagulation is necessary. Due to the fact that the suction tube embodied as a hollow profile simultaneously stiffens the fixed forceps leg, it may itself be provided with a reduced cross-section, so that the overall dimension of the fixed forceps leg with the hollow profile remains within the desired limits primarily required for inserting the coagulation forceps into tight body openings.

BRIEF DESCRIPTION OF THE DRAWINGS

In the following, an exemplary embodiment of the invention is described in greater detail using the drawings. Shown in partially schematic representation are:

FIG. 1 is a schematic representation of bipolar coagulation forceps with angled forceps legs according to the invention with a hollow profile being provided at the lower or exterior side of the fixed forceps leg at the side facing away from the gripping surface, which has an extension aligned along the hollow shaft, with a suction connection being provided at its proximal end, FIG. 2 is an enlarged scale detail of a portion of FIG. 1 marked by the circle B, namely the two adjacent forceps legs, with the upper forceps leg in reference to a pivot support being pivotal away from the fixed forceps leg, and simultaneously the entry opening of the hollow profile provided at the fixed forceps leg being clearly discernible.

DETAILED DESCRIPTION OF THE PREFERRED EMBODIMENTS

Figure 3:
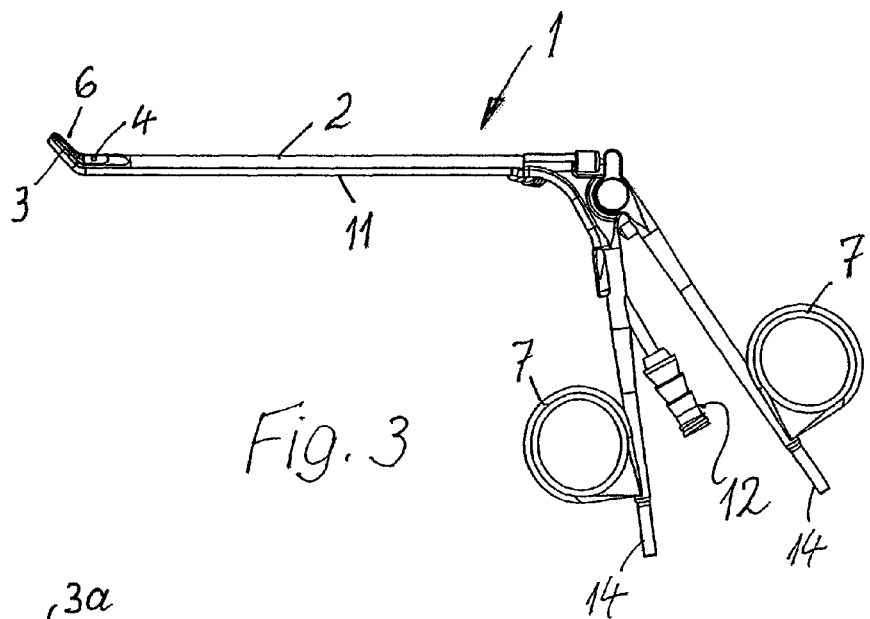
FIG. 3 is a side view of the pair of coagulations forceps.

Bipolar coagulation forceps referred to as 1 in their entirety are provided with a hollow shaft 2, an angled fixed forceps leg 3 provided with a gripping surface 3a, as well as a forceps leg 6 pivotable at a pivot support 4 in reference to the fixed forceps leg 3 by way of a pivoting element 5. Accordingly, finger or hand grips 7 are provided as well so that by the relative pivotal motion of one grip 7 in reference to the other one, the pivotal motion of the forceps leg 6 in reference to the forceps leg 3 can be achieved.

Figure 4:
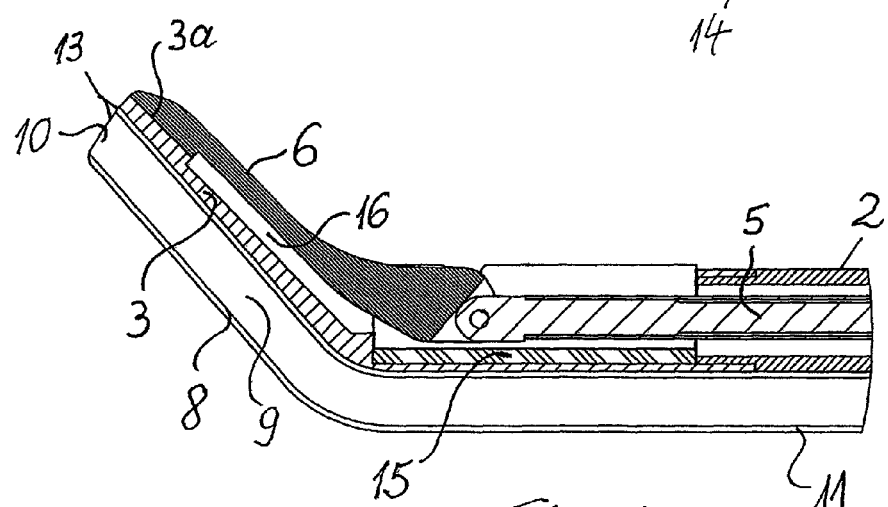
FIG. 4 is a longitudinal cross-section of the end region of the coagulation forceps shown in FIG. 2 with the two forceps legs and the hollow profile as well as insulation provided in an area of the pivot support of the pivotal forceps leg to the fixed forceps leg, in order to allow the coagulation forceps to be provided as a bipolar instrument.

Primarily in FIGS. 2 and 4 it is discernible that at the exterior side or the bottom side of the fixed forceps leg 3, facing away from the pivotal forceps leg 6, a hollow profile 8 is provided, by which the overall cross-section of the hollow profile 8 is reinforced and stiffened. This hollow profile 8 is open with its interior longitudinal cavity 9 in an end region of the forceps leg 3, thus having a mouth 10, and extends with an extension 11 along the hollow shaft 2. At the proximal end of the extension 11 of the hollow profile 8, a suction connector 12 is provided so that the hollow profile 8 not only stiffens the fixed forceps leg 3 but simultaneously allows suction to be provided in an area of the working tips of the forceps legs 3 and 6, when vacuum is applied to the suction connector 12. Thus, an area bleeding and to be treated can be kept free from exiting blood at all times so that the surgeon can see more easily through an endoscope, for example, where to perform coagulation.

Here, the hollow profile 8 ends in an area of the distal free end of the fixed forceps leg 3 and extends therefrom over the entire longitudinal extension of the forceps leg 3. Thus, on the one hand, the forceps leg 3 can be stiffened over its entire length and, on the other hand, suction can be applied to the farthest end of the forceps legs 3 and 6.

The hollow profile 8, preferably in the form of a tube or cannula, can be connected in one piece with the extension 11, as clearly discernible in FIGS. 2 and 4. However, it is also possible to weld the hollow profile positioned at the fixed forceps leg 3 to an extension 11 extending to the suction connector 12.

The entry opening 10, above also called the mouth, provided at the open end of the hollow profile 8, can be approximately flush with the distal end of the gripping surface 3a of the fixed leg 3, according to FIGS. 2 and 4. Thus, in this area no disturbing steps or overhangs are formed and simultaneously suction can become effective immediately at the distal end of the forceps legs 3 and 6.

The encircling rim 13, i.e. the face of the mouth or entry opening 10 into the hollow profile 8, is formed in one plane, according to FIG. 4, which forms an angle with the plane of the gripping surface 3a, which in this case is smaller than 90°. The part of the rim 13 facing away from the gripping surface 3a is therefore slightly offset backwards in reference to the end of the gripping surface 3a. This results in the hollow profile 8 with the gripping surface 3a at the distal end region being provided with a diagonal or conically narrowing form, which facilitates the introduction into tight body openings. The cross-section of the hollow profile 8 is circular in the exemplary embodiment; however, it could also be oval or slightly flattened.

The hollow profile 8 is fixedly connected to the fixed leg 3, in particularly soldered or welded, however it could also be connected in one piece, in order overall to have a sufficient stiffness with dimensions as small as possible.

In the exemplary embodiment, the coagulation forceps 1 are formed as bipolar coagulation forceps and in the area of the grips 7, the power connectors 14 are provided. Furthermore, in FIG. 4, it is discernible that an insulation 15 in the form of an insulating strip is provided between the fixed forceps leg 3 and the support 4 of the movable forceps leg 6, in order to avoid a short-circuit in this area. Here the insulation 15 insulates the non-angled part of the fixed forceps leg 3 and is connected thereto, as clearly discernible in FIG. 4. Due to the fact that the two forceps legs 4 and 6 are additionally provided with a distance 16 in reference to one another, except in the area of the gripping surfaces 3a, an effective bipolar coagulation is possible.

The pair of coagulation forceps 1 with the hollow shaft 2 and with a fixed forceps leg 3 provided with a gripping surface 3a at an angle in reference to the hollow shaft 2, as well as with a forceps leg 6, arranged pivotally thereto at a pivot support 4, is provided at the exterior or bottom side of the fixed forceps leg 3 facing away from the movable forceps leg 6 with a hollow profile 8 stiffening or reinforcing it. The hollow profile 8 is provided at a distal end of its interior longitudinal cavity 9 with a mouth or entry opening 10, i.e. is open and leads to a suction connector 12, so that via the hollow profile 8, suction can be applied in the distal end region of the forceps legs 3 and 6.

The invention claimed is:

1. Coagulation forceps (1) comprising a hollow shaft (2) with a fixed forceps leg (3) having a gripping surface (3*a*) set at an angle in reference to the hollow shaft (2), a pivotable forceps leg (6) pivotably connected at a pivot support (4) relative to the fixed forceps leg (3) by a pivotal element (5), the fixed forceps leg (3) is stiffened or reinforced by a hollow profile (8) arranged at an exterior or bottom side thereof facing away from the movable forceps leg (6), the hollow profile is open with an interior longitudinal cavity (9) in an end region of the fixed forceps leg (3) and extends towards the hollow shaft (2) and with an extension (11) along the hollow shaft (2), and is provided at a proximal end of the extension (11) with a suction connector (12), the coagulation forceps (1) comprise bipolar coagulation forceps and an insulation part (15) is provided between the fixed forceps leg (3) and the pivot support (4) for the movable forceps leg (6), and the hollow profile (8) and the extension (11) are connected in one piece or are welded together along an entire longitudinal extension thereof.

2. Coagulation forceps according to claim 1, wherein the hollow profile (8) ends in an area of the distal end of the fixed forceps leg (3) and extends therefrom over the entire longitudinal extension of the forceps leg (3).

3. Coagulation forceps according to claim 1, wherein an entry opening (10) at the open end of the hollow profile (8) is approximately flush to a distal end of the gripping surface (3*a*) of the fixed leg (3).

4. Coagulation forceps according to claim 3, wherein an encircling rim (13) of the entry opening (10) of the hollow profile (8) is arranged in one plane which forms an angle with a plane of the gripping surface (3*a*), which is equal to or smaller than 90°.

5. Coagulation forceps according to claim 4, wherein the rim of the entry opening of the hollow profile facing away from the gripping surface (3*a*) is off-set backwards in reference to an end of the gripping surface (3*a*), and the hollow profile (8) together with the gripping surface (3*a*) have a sloped or conically narrowing form.

6. Coagulation forceps according to claim 1, wherein a cross-section of the hollow profile (8) is circular or oval.

7. Coagulating forceps according to claim 1, wherein the hollow profile (8) is flattened or provided with an oval cross-section at at least a distal end or in a progression along the fixed forceps leg (3), and a larger dimension of the cross-section is arranged approximately parallel to the gripping surface (3*a*) and is approximately equivalent to or smaller than a width of the gripping surface (3*a*) of the fixed leg (3).

8. Coagulation forceps according to claim 1, wherein the hollow profile (8) is connected in a fixed manner to the fixed forceps leg (3).

9. Coagulation forceps according to claim 8, wherein the hollow profile (8) is connected to the fixed forceps leg (3) by soldering or welding.

10. Coagulation forceps according to claim 1, wherein the fixed forceps legs (3) and the hollow profile (8) are connected in one piece or have a connection point along the hollow profile (11) extending along the hollow shaft (2).

11. Coagulation forceps according to claim 1, wherein the insulation (15) shields at least the non-angled part of the fixed forceps leg (3).

12. Coagulation forceps according to claim 11, wherein the insulation (15) is connected to the non-angled part of the fixed forceps leg (3).

* * * * *